United States Patent [19]

Metz

[11] Patent Number: 4,593,044
[45] Date of Patent: Jun. 3, 1986

[54] INJECTABLE SOLUTION FOR THE TREATMENT OF INFLAMMATIONS

[75] Inventor: Gunter Metz, Blaubeuren, Fed. Rep. of Germany

[73] Assignee: Merckle GmbH, Fed. Rep. of Germany

[21] Appl. No.: 636,333

[22] Filed: Jul. 31, 1984

[30] Foreign Application Priority Data

Aug. 5, 1983 [DE] Fed. Rep. of Germany ....... 3328401

[51] Int. Cl.$^4$ .................. A61K 31/19; A61K 31/195; A61K 31/13
[52] U.S. Cl. .................................... 514/557; 514/561
[58] Field of Search ............... 424/317, 319; 514/557, 514/561

[56] References Cited

U.S. PATENT DOCUMENTS

| 2,101,867 | 12/1937 | Miller et al. | 424/319 |
| 3,832,465 | 8/1974 | Ghadimi | 424/319 |
| 3,845,210 | 10/1974 | Sato et al. | 424/274 |
| 3,876,801 | 4/1975 | Tixier | 424/319 |
| 4,241,086 | 12/1980 | Iwao et al. | 424/319 |
| 4,486,436 | 12/1984 | Sunshine et al. | 424/317 |

Primary Examiner—Ronald W. Griffin
Attorney, Agent, or Firm—Robbins & Laramie

[57] ABSTRACT

The invention relates to the use of naproxen lysinate, ketoprofen lysinate and/or diclofenac lysinate in the form of an injectable solution in the treatment of inflammations and rheumatic disorders, and to injectable solutions containing the anti-inflammatory active compound naproxen, ketoprofen or diclofenac in the form of its lysinate.

16 Claims, No Drawings

INJECTABLE SOLUTION FOR THE TREATMENT OF INFLAMMATIONS

Injection solutions for the treatment of acute inflammations and rheumatic disorders are predominately combination preparations based on anti-inflammatory active compounds, for example, phenylbutazone and salicylic acid derivatives. The incorporation of these into physiologically tolerated solutions presents no problems. In addition, combinations with corticoids are particularly common, but there are therapeutic limits to the use of these.

Among the accepted potent, anti-rheumatically active single substances, such as indometacin, ketoprofen, naproxen, ibuprofen and diclofenac, only diclofenac-sodium is known in a ready-to-use injection solution. Indometacin and ketoprofen are currently available for therapeutic use only in the form of dry lyophilizates. This is due to the fact that, on the one hand, a relatively high pH is required for solubilization with an inorganic base, e.g., sodium hydroxide, while on the other hand, the active compounds suffer decomposition and give unstable formulations at this pH.

It is the object of the invention to prepare a stable and physiologically tolerated ready-to-use injection solution with as high an active compound content as possible in a small volume. The selection of suitable active compounds was restricted to ketoprofen, naproxen and diclofenac. Although it is very potent, indometacin has a high degree of side effects, and thus was not selected. Ibuprofen was not selected because it has the weakest action among the active compounds mentioned and hence, very high concentrations in the injection solution and also large volumes would be required to achieve therapeutic effects. We have found that the object of the invention is achieved by the use of the lysinates of ketoprofen, naproxen and diclofenac. The solutions of the lysinates are easy to prepare and have the advantage, over the corresponding solutions of the sodium salts, that their pH is in the physiological range, that they permit substantially higher active compound concentrations to be achieved, and that the solutions thus obtained are stable. In experimental investigations we have further found, surprisingly, that the pharmacological effect of the lysinate solution is significantly superior to that of a solution of the corresponding sodium salt.

Ketoprofen, naproxen and diclofenac are the internationally accepted trivial names for the following active components:
Ketoprofen: 2-(3-benzoylphenyl)-propionic acid
Naproxen: 2-(6-methoxy-2-naphthyl)-propionic acid
Diclofenac: [2-(2,6-dichloro-anilino)-phenyl]-acetic acid Lysine is an amino acid, chemical name 2,6-diaminocaproic acid, which according to the invention is preferably employed in the naturally occurring L-form. Lysinates are salts of lysine.

The activity of the solutions according to the invention compared to corresponding solutions of the sodium salts was determined by a modified method of Coubon et al, 1954 (R. A. Turner, "Screening Methods in Pharmacology", Academic Press, New York, 1965, page 157) on the rat paw kaolin edema (seven animals/group). The provoking agent, kaolin, was administered subcutaneously as a 20% strength aqueous suspension, in a volume of 0.2 ml/paw, into the right rear paw. One hour after its administration, the test solution was administered intramuscularly into the right thigh. The control group was given the vehicle only. Twenty-four hours after administration, the edema formation was measured from the water displacement, using conventional methods. The results summarized in the table below were achieved:

|  |  | Amount of Active Compound (mg/kg) | Edema Reduction* |
|---|---|---|---|
| Naproxen |  |  |  |
|  | lysinate | 1.0 naproxen | −14% |
|  |  | 10.0 naproxen | −44.8%** |
|  | sodium | 2.0 naproxen | +2% |
|  |  | 20.0 naproxen | −49.1%** |
| Ketoprofen |  |  |  |
|  | lysinate | 1.0 ketoprofen | −48.3%** |
|  |  | 10.0 ketoprofen | −48.3%** |
|  | sodium | 2.0 ketoprofen | −23.3% |
|  |  | 20.0 ketoprofen | −74.1%** |
| Diclofenac |  |  |  |
|  | lysinate | 0.75 sodium diclofenac | −1.7% |
|  |  | 7.5 sodium diclofenac | −44.8%** |
|  | sodium | 10 sodium diclofenac | −10.3% |
|  |  | 20 sodium diclofenac | −39.7%** |

*Based on control group (100%)
**Significance $p < 0.001$

As the results show, the anti-inflammatory effect of the lysinates used, compared to those of the sodium salts, is either significantly superior at a substantially lower active compound concentration (ketoprofen, diclofenac) or is of equal potency (naproxen).

The novel injection preparations are preferably prepared by dissolving the isolated lysinates. The lysinates can be formed by reacting the sodium salts of naproxen, diclofenac and ketoprofen with lysine hydrochloride in suitable solvents using conventional methods. Thereafter, the crystalline lysinates can be prepared in a pure form by crystallization from suitable solvents.

Moreover, the reaction of the dissolved sodium salts with equimolar amounts of lysine hydrochloride can be carried out directly in the finished injection solution, rather than first isolating the lysinates formed, provided that the sodium chloride formed in this direct method does not exceed physiologically acceptable levels.

The reaction and solubilization of the active compounds with lysine base directly in the injection solution is also feasible but not very advantageous. Since lysine base itself tends to intrinsic discoloration and decomposition, the use of the stable lysine hydrochloride is preferred to the use of the base.

The solvent used is injection-quality water, by itself or preferably with the addition of conventional, physiologically tolerated solvents and/or solubilizing agents, e.g., propylene glycol, polyols such as glycerol, polyoxyalkylenes, e.g., poly(oxyethylene)-poly(oxypropylene) polymers, glycerol-formal, benzyl alcohol or butanediol. As is known, the addition of these solubilizing agents produces solutions which are stable at low temperatures and do not lead to partial crystallization of the active compounds, in spite of the high concentration of active compound.

Furthermore, as is customary for injection preparations, oxidation stabilizers, e.g., sodium bisulfite or preservatives, e.g., benzyl alcohol, may advantageously be incorporated. For therapeutic use, the addition of local anesthetics, e.g., lidocaine or cinchocaine, is advisable.

For therapeutic use, the injection preparations according to the invention are sterilized by conventional methods or filled under sterile conditions into a 1-3 ml ampules.

The injection solutions according to the invention contain, when naproxen lysinate or ketoprofen lysinate is used, 5-25%, preferably 10-15%, of naproxen and ketoprofen, respectively, and when diclofenac lysinate is used, 2-5% of diclofenac. The therapeutically useful individual dose of the lysinates is 100-300 mg for naproxen or ketoprofen and 40-100 mg for diclofenac.

The examples which follow explain the injection solutions according to the invention in more detail.

EXAMPLE 1

10.0 g of ketoprofen
7.16 g of L-lysine.HCl
39.0 ml of N NaOH
1.0 g of benzyl alcohol
0.5 g of lidocaine.HCl made up to 100 ml with doubly distilled water.

EXAMPLE 2

16.34 g of naproxen lysinate (corresponding to 10.0 g of naproxen)
3.0 g of poly(oxyethylene)-poly(oxypropylene) polymer (molecular weight 8350)
1.0 g of benzyl alcohol
0.25 g of sodium bisulfite made up to 100 ml with doubly distilled water.

EXAMPLE 3

3.75 g of diclofenac sodium
2.15 g of L-lysine hydrochloride
60.0 ml of propylene glycol
1.0 g of benzyl alcohol made up to 100 ml with doubly distilled water.

What is claimed is:

1. An anti-inflammatory injectable solution consisting essentially of an effective amount of an anti-inflammatory active compound selected from the group consisting of naproxen, ketoprofen and diclofenac in the form of its lysinate and a pharmaceutically acceptable diluent, wherein said solution is stable and has a pH in the physiological range.

2. The injection solution of claim 1, comprising 5-25% by weight of ketoprofen in the form of ketoprofen lysinate.

3. The injection solution of claim 2, comprising 10-15% by weight of ketoprofen in the form of ketoprofen lysinate.

4. The injection solution of claim 1, comprising 5-25% by weight of naproxen in the form of naproxen lysinate.

5. The injection solution of claim 4, comprising 10-15% by weight of naproxen in the form of naproxen lysinate.

6. The injection solution of claim 1, comprising 2-5% by weight of diclofenac in the form of diclofenac lysinate.

7. The injection solution of claim 1, in the form of an aqueous solution or of an aqueous solvent mixture which further comprises physiologically tolerated solubilizing agents, stabilizers or preservatives.

8. The injection solution of claim 7, comprising 5-25% by weight of ketoprofen in the form of ketoprofen lysinate.

9. The injection solution of claim 8, comprising 10-15% by weight of ketoprofen in the form of ketoprofen lysinate.

10. The injection solution of claim 7, comprising 5-25% by weight of naproxen in the form of neproxen lysinate.

11. The injection solution of claim 10, comprising 10-15% by weight of naproxen in the form of naproxen lysinate.

12. The injection solution of claim 7, comprising 2-5% by weight of diclofenac in the form of diclofenac lysinate.

13. A method for the treatment of inflammations and rheumatic disorders which comprises the administration of an anti-inflammatory injectable solution which consists essentially of an effective amount of an anti-inflammatory active compound selected from the group consisting of naproxen, ketoprofen and diclofenac in the form of its lysinate and a pharmaceutically acceptable diluent, wherein said solution is stable and has a pH in the physiological range.

14. The method of claim 13, wherein said compound is naproxen lysinate.

15. The method of claim 13, wherein said compound is ketoprofen lysinate.

16. The method of claim 13 wherein said compound is diclofenac lysinate.

* * * * *

REEXAMINATION CERTIFICATE (873rd)

United States Patent [19]

Metz

[11] B1 4,593,044

[45] Certificate Issued Jun. 21, 1988

[54] INJECTABLE SOLUTION FOR THE TREATMENT OF INFLAMMATIONS

[75] Inventor: Gunter Metz, Blaubeuren, Fed. Rep. of Germany

[73] Assignee: Merckle GmbH, Fed. Rep. of Germany

Reexamination Request:
No. 90/001,248, May 22, 1987

Reexamination Certificate for:
Patent No.: 4,593,044
Issued: Jun. 3, 1986
Appl. No.: 636,333
Filed: Jul. 31, 1984

[30] Foreign Application Priority Data

Aug. 5, 1983 [DE] Fed. Rep. of Germany ....... 3328401

[51] Int. Cl.$^4$ .................. A61K 31/19; A61K 31/195; A61K 31/13
[52] U.S. Cl. ..................................... 514/557; 514/561
[58] Field of Search ................ 514/557, 561; 424/317, 424/319

[56] References Cited

U.S. PATENT DOCUMENTS

3,904,682 9/1975 Fried et al. .
4,279,926 7/1981 Bruzzese et al. .

FOREIGN PATENT DOCUMENTS

826446 6/1975 Belgium .
882889 8/1980 Belgium .
1497094 1/1978 United Kingdom .

OTHER PUBLICATIONS

Annual Drug Data Report (1981), p. 136 (T. R. Prous).
Ibanez, et al., Arch. Farmacol. Toxicol. (1980) 6(2), pp. 145–150. Chem. Abstr. 94:52802y (1980).

*Primary Examiner*—Ronald W. Griffin

[57] ABSTRACT

The invention relates to the use of naproxen lysinate, ketoprofen lysinate and/or diclofenac lysinate in the form of an injectable solution in the treatment of inflammations and rheumatic disorders, and to injectable solutions containing the anti-inflammatory active compound naproxen, ketoprofen or diclofenac in the form of its lysinate.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 2-5, 8-11, 14 and 15 are cancelled.

Claims 1, 6, 12, 13 and 16 are determined to be patentable as amended.

Claim 7, dependent on an amended claim, is determined to be patentable.

1. An anti-inflammatory injectable solution consisting essentially of an effective amount of [an] *the* anti-inflammatory active compound [selected from the group consisting of naproxen, ketoprofen and] diclofenac [in the form of its lysinate] *L-lysinate* and a pharmaceutically acceptable diluent, wherein said solution is stable and has a pH in the physiological range.

6. The injection solution of claim 1, comprising 2-5% by weight of diclofenac in the form of diclofenac [lysinate] *L-lysinate*.

12. The injection solution of claim 7, comprising 2-5% by weight of diclofenac in the form of diclofenac [lysinate] *L-lysinate*.

13. A method for the treatment of inflammations and rheumatic disorders which comprises the administration of an anti-inflammatory injectable solution which consists essentially of an effective amount of [an] *the* anti-inflammatory active compound [selected from the group consisting of naproxen, ketoprofen and] diclofenac [in the form of its lysinate] *L-lysinate* and a pharmaceutically acceptable diluent, wherein said solution is stable and has a pH in the physiological range.

16. The method of claim 13 wherein said compound is diclofenac [lysinate] *L-lysinate*.

* * * * *